United States Patent [19]

Visuri

[11] Patent Number: 4,699,882
[45] Date of Patent: Oct. 13, 1987

[54] STABLE GLUCOSE ISOMERASE CONCENTRATE AND A PROCESS FOR THE PREPARATION THEREOF

[75] Inventor: Kalevi J. Visuri, Kantvik, Finland

[73] Assignee: Suomen Sokeri Oi, Finland

[21] Appl. No.: 749,684

[22] Filed: Jun. 25, 1985

[51] Int. Cl.$^4$ .......................... C12N 9/96; C12N 9/92
[52] U.S. Cl. ..................................... 435/188; 434/234
[58] Field of Search ................................ 435/234, 188

[56] References Cited

U.S. PATENT DOCUMENTS

| | | |
|---|---|---|
| 2,773,002 | 12/1956 | Connors et al. |
| 3,133,001 | 5/1964 | Muset et al. |
| 3,242,056 | 3/1966 | Dubois-Prevost |
| 3,413,198 | 11/1968 | Deutsch |
| 3,515,642 | 6/1970 | Mima et al. |
| 3,637,640 | 1/1972 | Huber |
| 3,666,627 | 5/1972 | Messing |
| 4,152,211 | 5/1979 | Nielsen et al. |
| 4,237,231 | 12/1980 | Jackson et al. ...................... 435/234 |
| 4,331,761 | 5/1982 | Dawson et al. |
| 4,451,569 | 5/1984 | Kobayashi et al. |
| 4,618,584 | 10/1986 | Johnson et al. ...................... 435/234 |

FOREIGN PATENT DOCUMENTS

| | | |
|---|---|---|
| 1004614 | 2/1977 | Canada ............................... 435/234 |
| 1076750 | 7/1968 | United Kingdom |
| 1389147 | 4/1975 | United Kingdom |
| 2090599 | 7/1982 | United Kingdom |

OTHER PUBLICATIONS

Methods in Enzymology, vol. 104, pp. 370–381 (1984).
Nesterenko et al., Biological Abstracts, vol. 73(5), 31523.
Phosphoglucose Isomerase II Mammary Gland, F. J. Reithel, Chem. Abst. 67:9129, Abs. No. 97151u, (1967).
Stable, Highly Active Glucose Isomerase Concentrate. Okada, Tsutomu and Tadamasa, Chem. Abst. 87:241, Abs. No. 179915y (1977).
Stabilities of Enzymes in Polyhydric Alcohols, Yasumatsu, K. et al., Agr. Biol. Chem., 29(7): 665–671 (1954).
The Effects of Polyhydric and Monohydric Alcohols on the Heat Induced Reversible Denaturation of Chymotrypsinogen A, Gerlsma, S. Y., Eur. J. Biochem., 14: 150–153 (1970).
Stable Aqueous Preparations of Digestion Enzymes, Hatano, M. et al., Chem. Abst. 68: 81420 (1968), Abst. No. 81410n.

Primary Examiner—Lionel M. Shapiro
Attorney, Agent, or Firm—Scully, Scott, Murphy & Presser

[57] ABSTRACT

The invention concerns a stable glucose isomerase concentrate, in which the glucose isomerase is present as dissolved in a concentrated polyhydroxy compound containing water solution. The invention also concerns a process for the preparation of such a glucose isomerase concentrate, whereby (a) a suitable salt is added to a partially purified glucose isomerase solution obtained from fermentation, so as to crystallize the glucose isomerase, (b) the solution is cooled so as to promote crystallization of the glucose isomerase, and the crystal mass formed is separated, whereupon, if desired, one or several recrystallizations are performed, and (c) a carbohydrate or a concentrated water solution of same is added to the crystal mass obtained, which said mass is dissolved, whereby a stable glucose isomerase concentrate is obtained. The glucose isomerase concentrate in accordance with the invention is used for immobilizing the glucose isomerase on a carrier material.

18 Claims, No Drawings

STABLE GLUCOSE ISOMERASE CONCENTRATE AND A PROCESS FOR THE PREPARATION THEREOF

The present invention relates to a concentrate of a glucose isomerase enzyme which is chemically and microbiologically stable without addition of microbicides and which is very useful as such for the immobilization of the enzyme onto a carrier material in a reactor column. The enzyme also relates to a process for the preparation of such a concentrate.

The use of a glucose isomerase for the isomerization of glucose to fructose is a well known industrial process, in which the enzyme is often used in the immobilized form. In many of the commercial processes that are in use, the immobilized enzyme preparation is prepared as a separate process, in which either the enzyme is immobilized on the carrier by means of the adsorption technique or the entire microbial cell mass with the enzyme is immobilized to make a matrix. The reactor column is made up of ready immobilized enzyme. When the enzyme has been used up, the column is emptied and again made up of fresh immobilized enzyme preparation.

It is known that a purified enzyme is adsorbed on a carrier much better than a non-purified crude preparation (U.S. Pat. No. 4,347,322). The problem has been to prepare such a stable, easy-to-handle and easy-to-store enzyme preparation, which can be used for immobilizing the enzyme on the carrier in a column.

A precipitate or crystal mass obtained from glucose isomerase purification processes based on precipitation or crystallization contains at least 60 per cent by weight of water, which cannot be removed without destruction of the enzyme structure. The crystal mass as such is not microbiologically stable, and it is difficult to handle and to dose. An alternative is dissolution of the crystal mass to a solution, the concentration of which should preferably be as high as possible, in view of storage, stability and transport the obvious procedure would be to dissolve the enzyme crystals in water or in a dilute salt solution. In practice, however, it has been discovered that, owing to the relatively low solubility of glucose isomerase, it is not possible to prepare a sufficiently concentrated solution of the isomerase by dissolving crystals in water. A diluted water solution of the isomerase is highly unstable and loses its activity as a result of microbiological and chemical deterioration in a few days.

It has also been suggested that the enzyme could be dissolved in a organic solvent (U.S. Pat. No. 4,077,842). However, it is not advisable to use organic solvents in a process of food production, wherefore this technique is poorly suited for an enzyme that is used directly for the preparation of foods. However, if the enzyme were not to be employed in food, the kinds of substances which would be useful for dissolution may be expanded.

There is an abundance of literature concerning the preparation, purification and use of glucose isomerase, because glucose isomerase is one of the most important enzymes at present in use. However, all the published purification processes are quite complicated and, as a rule, give rather low yields.

The purification of enzymes and proteins by means of crystallization is, in itself, well known, and, for example, in the manual *Enzymes* (Dixon, M. and Webb, E.C., *Enzymes*, 3rd ed., Longman Group Ltd., Bungay 1979, 1116 p.) 192 photographs are shown of enzyme crystals. Moreover, it is known that ammonium sulfate is in several cases suitable as an agent that induces crystallization and reduces solubility. In addition, ammonium sulfate crystallization can often be carried out by means of some other salt or organic solvent, such as acetone or alcohol. In this field of chemistry, it is generally admitted that it is never self-evident that any particular enzyme or any other protein may be crystallized by means of some, in itself well known, precipitant. Numerous proteins and enzymes are known whose crystallization has not been successful as yet, even though the purification processes in biochemistry have undergone an immense developement. Thus, the "science" of enzyme crystallization (which in reality may be more of an art) is highly empirical and just because certain procedures are shown to be successful for crystallizing one enzyme does not mean those same procedures have general applicability for the crystallization of other enzymes.

The use of fractional sulfate precipitation (ammonium and/or magnesium sulfate) as a purification process for glucose isomerases or as a part of such a process is known from several publications (U.S. Pat. No. 4,237,231, U.S. Pat. No. 4,077,842, *Agr. Biol. Chem.*, 45 (1981) 619–627, id. 28 (1965) 1123–1128, id. 34 (1970) 1795–1804, id. 29 (1965) 1129–1134, *Biochem. Biophys. Acta.*, 151 (1968) 670–680).

The sulfate concentrations used in these purification processes for isomerases have been relatively high. For example, in the process in accordance with the U.S. Pat. No. 4,237,231, the unneccessary proteins are first precipitated from the isomerase solution at the saturation degree of 40% ammonium sulfate, and then the isomerase itself is precipitated at a higher saturation degree (up to 60%).

When high ammonium sulfate concentrations are used in fractional precipitation, an abundance of other proteins always precipitate along with the isomerase; the higher the concentration of ammonium sulfate used, the more additional proteins will precipitate, unless the isomerase has already been prepurified in some way by some other method.

In purification processes based on fractional precipitation, the result is usually an amorphous precipitate, which is very difficult or even impossible to separate from the mother liquor in good yield by means of centrifuges or separators intended for industrial use.

The amorphous precipitate is, as a rule, a mixed deposit, which, besides the isomerase, also contains other proteins, particularly if the raw material is a microbial-cell liquid, which has not been pre-purified. Such an amorphous precipitate is difficult to separate from the mother liquor, and precipitation does not give the desired purification effect with respect to the isomerase.

Crystallization of glucose isomerases by means of ammonium sulfate, other salts, or organic solvents have been described in several publications *(Biophys. Acta,* 151 (1968) 670–680, *Agr. Biol. Chem.*, 34 (1970) 1795–1804, id. 45 (1981) 619–627, id. 33 (1969) 1527–1534). Characteristic features of the crystallization processes described in said publications are low yield, very long crystallization time, or relatively high consumption of chemicals. In all of these cases, the aim has been to prepare a small quantity of pure isomerase for basic research purposes. Thus, the isomerase has first been purified by means of some method (extraction with an organic solvent, DEAE-Sephadex-column chromatography, ammonium sulfate precipitation, dialysis), whereupon crystallization of purified isomerase from pure water solution has been carried out with ammonium sulfate, phosphate buffer, or acetone.

None of the processes described in the above publications has been used on an industrial scale, because of their poor economy.

The present invention relates to a stable glucose isomerase concentrate, which is characterized in that it contains glucose isomerase dissolved in a concentrated aqueous polyhydroxy compound containing solution.

It has been found that the concentrate according to the invention is both chemically and microbiologically stable, and particularly useful in processes in which the glucose isomerase is immobilized to a carrier material. Suitable poly-hydroxy-containing compounds are all such compounds which are readily soluble in water, such as carbohydrates and polyols. Sugars, glycerol, polypropylene glycol or ethylene glycol are also suitable. Particularly suitable are sugars that are used as foods as such, as well as sugar alcohols which are allowed as food additives. Since the end product of isomerization is a glucose-fructose syrup, the mixture of these sugars, i.e., invert sugar, is excellently suitable for the purpose.

The total dry solds content in the concentrate must be such that it is in itself microbiologically stable, i.e., the dry solids content should be about 60 to 70 per cent by weight (i.e., the activity of the water must be sufficiently low).

The glucose isomerase concentrate according to the invention contains 5 to 20 weight percent glucose isomerase, preferably contains 5 to 15 wt. percent of glucose isomerase, 30 to 60 wt. percent of a carbohydrate soluble in water, such as glucose, maltose, fructose, saccharose, sorbitol, xylitol, or of a mixture thereof, e.g., invert sugar, glucose syrup or isomerized glucose syrup, no more than 15 wt. percent of an appropriate salt, such as ammonium and/or magnesium sulfate, and/or a buffer (pH 5.0 to 8.0), e.g., sodium-potassium-phosphate buffer, carbonate buffer, or a buffer made of an organic salt (e.g., salt of an amino acid) or a mixture of buffers, and balance water.

The pH of the concentrate is 5.0 to 8.0 and enzyme activity is 500-10,000 GIU/g concentrate, preferably pH 6.0 to 8.0, and the enzyme activity is to 5000 GIU/g concentrate (GIU=glucose isomerase units).

In the following, some examples are given of suitable enzyme concentrates according to the invention:

1.

50 wt. % glycerol
10 wt. % water
15 wt. % enzyme
5 wt. % ammonium sulfate

2.

50 wt. % invert sugar
30 wt. % water
15 wt. % enzyme
1 wt. % buffer (Na-K-phosphate)
4 wt. % ammonium sulfate

3.

50 wt. % sorbitol
40 wt. % water
10 wt. % enzyme

4.

50 wt. % saccharose
30 wt. % water
15 wt. % enzyme
5 wt. % buffer (sodium phosphate)

The composition of the concentrate may, however, be varied as required, while taking care that the total concentration is sufficiently high and the solution, yet, in liquid form is easy to handle.

The glucose isomerase concentrates according to the invention are pure, stable, and easy to handle and dose. The enzyme activity can be adjusted. In view of the use, a suitable range of activity is 2000 to 10,000 GIU/g preparation.

The sugars, sugar alcohols and salts to be used are preferably of food grade (e.g., Food Chemicals Codes standard). The enzyme shall be purified adequately by crystallization or by any other method.

A suitable carrier material for the adsorption of glucose isomerase is a material with anion-exchange capacity, e.g., glass beads, ion-exchange resin or a silica-based carrier. Particularly suitable are diethylaminoethyl (DEAE) derivatives, which are known to adsorb proteins, such as DEAE-cellulose and DEAEdextran. There is a large number of carrier materials described in the literature.

When DEAE cellulose is used as carrier, it is easy to attain an activity higher than 1000 IGIU/g immobilized enzyme. (IGIU=immobilized glucose isomerase activity).

The invention also relates to a process for the preparation of the stable glucose isomerase concentrate described above. The process is characterized by:

(a) adding a suitable salt to a partially-purified glucose isomerase solution obtained from fermentation, so as to crystallize the glucose isomerase, (b) cooling the solution so as to promote crystallization of the glucose isomerase, and separating the crystal mass formed, and then, if desired, effecting one or several recrystallizations, and (c) adding a carbohydrate or a concentrated water solution thereof to the obtained crystal mass, which dissolves, whereby a stable glucose isomerase concentrate is obtained.

According to the present invention, the isomerase enzyme can be purified highly efficiently by crystallizing it from a salt solution. Suitable salts are all such non-toxic salts which do not inactivate the enzyme. In the process according to the present invention, ammonium and/or magnesium sulfate is used.

Precipitation of glucose isomerase by means of a salt is in itself a conventional procedure, being described, e.g., in *Aqr. Biol. Chem.*, 29 (1965) pp. 1129–1134 (Isumre and Sato). However, no such process has earlier been described in which the formation of crystals takes place. In the above cited process, an amorphous precipitate is formed.

Depending on the conditions, either an amorphous precipitate or a crystalline precipitate can be obtained from the isomerase by using the same chemical ammonium sulfate or magnesium sulfate. It is generally known that numerous enzymes behave in the same way.

A characteristic and surprising feature of the process according to the invention is that the isomerase precipitates as a crystalline substance and before all other substances that may precipitate. In the process, precisely selected conditions and such a low ammonium sulfate concentration are used that no other substances precipitate from the solution. In this respect, the process differs essentially from what has been described in the literature in this field. Previously, glucose isomerase has not been crystallized directly and alone as the only precipitating component from a cell liquid or a cell liquid concentrate of a production microbe. The process also gives a very high yield which differs essentially from what has been earlier stated in the literature.

It is generally known that the storage quality and stability of enzyme preparations can be increased, e.g., by means of glycerol, polyalcohols and sugars. Such enzyme preparations are usually prepared by adding the said substance to a concentrated enzyme solution.

It has surprisingly been found that when dry anhydrous polyalcohol or sugar (preferably glucose) is mixed into a concentrated isomerase crystal suspension or into a solid crystal mass having a highest possible activity of about 10,000 GIU/g, the isomerase crystals are dissolved and a genuine clear solution is produced. Such a solution is stable when its water concentration is sufficiently low and when its isomerase activity is sufficiently high. The solution may contain salts derived from the crystallization process or salts that have been added afterwards, which salts in themselves have an effect increasing the microbiological stability. The polyalcohol or sugar, however, has an essential importance in view of the dissolution of the isomerase crystals in order than an isomerase activity as high as possible could be attained for the solution.

In prior art, no examples have been given of isomerase solutions having as high an enzymatic activity as the product according to the present invention, nor have methods been described for the preparation of such solutions.

The preparation of the glucose isomerase concentrate is preferably carried out as follows:

(a) A cell liquid is prepared from the organism *Streptomyces rubiginosus* by means of lysis (U.S. Pat. No. 4,410,627), and from the cell liquid, by ultrafiltration, a concentrate containing isomerase is prepared for raw material for the crystallization process; a preferred isomerase concentration of the concentrate is 200 to 800 GIU/g.

(b) The pH of the isomerase solution is adjusted to the range of 5.7 to 8.0, preferably pH 7.0.

(c) The solution is cooled to 16° C. or below.

(d) Ammonium and/or magnesium sulfate is added to the solution, preferably 50 to 170 g per litre of solution. The sulfate quantity to be added depends on the original isomerase concentration and on the final temperature of crystallization. The most preferable quantity of sulfate to be added is such a quantity with which only the isomerase is crystallized but the other proteins do not yet start precipitating.

(e) The addition of the sulfates is preferably effected gradually so that the addition of the whole quantity takes 2 to 4 hours, even though an acceptable result may also be obtained by adding the whole quantity all at once, but in such a case the size of the isomerase crystals remains unfavourably small.

(f) The solution is cooled preferably during several hours, preferably close to the freezing point of the mixture concerned, the freezing point being at the lowest tested sulfate concentrations about $-2°$ C. and at the highest ones $-6°$ C.; the cooling may be started either simultaneously with the beginning of the sulfate addition or only upon completion of the sulfate addition; by means of a gradual cooling, a cooling-crystallization effect is obtained that increases the size of the isomerase crystals advantageously, besides the fact that cooling has a solubility lowering effect which again increases the yield.

(g) The isomerase crystals are separated from the solution by allowing them to settle to the bottom of the vessel, by filtering them or, on a large scale, most preferably, by centrifuging them by means of a continuous separator.

(h) The separated crystal mass is dissolved by adding to it a dry carbohydrate or its concentrated water solution, whereby the isomerase crystals are dissolved and a stable glucose isomerase concentrate is produced.

If desired, the crystallization may be repeated, in which case the crystal mass must be dissolved after the separation (step g) into an abundant quantity of water at a relatively high temperature (20 to 30° C.). In this connection, a suitable quantity of water is such that the isomerase activity of the solution is 500 to 2000 GIU/ml, in other words, the weight of the quantity of water used is typically 4 to 10 times the weight of the crystal mass.

As used herein, GIU is the abbreviation for glucose isomerase unit and is that amount of enzyme which will convert 1 micromole of glucose to fructose per minute in a solution initially containing 2 moles of glucose per liter, 0 02 moles of $MgSO_4$ and 0.001 moles of $CoCl_2$ per liter at a pH of 6.84 to 6.85 (0.2M sodium maleate) measured at ambient temperature, and at a temperature of 60° C. Glucose isomerase determinations were carried out by the method described by N. E. LLoyd, et al., Cereal Chem., 49, No. 5 pp. 544–553 (1972).

The following examples will illustrate the invention.

EXAMPLE 1

A bath of about 40 cubic meters of *Streptomyces rubiginosus* microbe was fermented as described in U.S. Pat. No. 4,410,627. The cell mass was was lysed in a known way (same reference). The cell residues and the other solid matter were removed by filtration by means of a conventional siliceousearth drum filter, whereby 32 tons of isomerase-containing filtrate was obtained. This filtrate was filtered by means of a PCI (Patterson-Candy, Inc.) ultrafilter, whereby 3000 kg of isomerase-containing concentrate was obtained, the activity of which was 960,000,000 GIU. The permeate that had passed through the ultrafiltration membrane was removed.

120 kg Magnesium sulfate and 300 kg ammonium sulfate ($(MgSO_4)7H_2O$ and $(NH_4)_2SO_4$, food grade) were added to the concentrate. The mixture was cooled to 10° C. in order to promote crystallization. The crystals formed were separated by decanting, and the crystallization was repeated by adding 411 kg ammonium sulfate. The crystals were again separated by decanting. The crystal mass was dissolved by adding 402 kg water, and the pH of the solution was adjusted, by means of a 1M ammonia solution to 6.5. The solution was filtered with a plate filter, and the crystallization was repeated once more by using 16 kg of magnesium sulfate and 40 kg of ammonium sulfate.

A yield of 90 kg of crystal mass, of which 29 kg was enzyme, 3.7 kg salts ($MgSO_4$, $(NH_3)_2SO_4$, and balance water, was obtained. To the crystal mass 45 kg of glucose and 45 kg of fructose as well as 20 kg of invert sugar having a dry solids content of 70 per cent by weight were added. In this way, 200 kg of an enzyme preparation was obtained, the composition of which was as follows:
- 29.2 wt. % water
- 52.0 wt. % sugars
- 14.5 wt. % glucose isomerase
- 4.3 wt. % salts (magnesium-ammonium sulfate)

The glucose isomerase activity of the enzyme concentrate was 4500 GIU/g.

EXAMPLE 2

An ultrafiltered fermentate was prepared in the way described in Example 1. To 4000 kg of ultrafiltered fermentate, 244 kg of crystalline ammonium sulfate solution in which 600 kg of salt had been dissolved into 900 kg of water. The solution was cooled to 13° C. and kept at this temperature for 20 hours. The crystal mass formed was separated by means of a Westfalia NA 7 separator. The crystals were dissolved into water, and the solution was filtered. The quantity of filtrate was 2000 liters. The crystallization was repeated by using 122 kg of crystalline ammonium sulfate and ammonium sulfate solution that contained 300 kg of ammonium sulfate as dissolved into 460 liters of water. The crystal mass obtained was again separated by means of a separator. To the crystal mass (525 kg), the same quantity of crystalline fructose was added, whereby the mass was dissolved and the fructose was partly isomerized to glucose. In this way, a stable enzyme concentrate was obtained, the composition of which as as follows:
- Sugars (glucose & fructose): 50.0 wt. %
- Enzyme: 11.2 wt. %
- Ammonium sulfate: 3.5 wt. %
- Water: 35.3 wt. %

The glucose isomerase activity of the concentrate was 3000 GIU per gram.

EXAMPLE 3

An ultrafiltered fermentate was prepared in the way described in Example 1. For the crystallization of the glucose isomerase 4000 litres of ultrafiltered fermentate having an activity of 2,400,000,000 GIU was used. The pH of the solution was adjusted by means of a 5% NaOH solution to pH 7.0, and the temperature of the solution was adjusted to 12° C. For the crystallization of the glucose isomerase, 500 kg of ammonium sulfate dissolved in 750 litres of water was added to the solution during two hours with an even rate of feed. Then the solution was cooled to −2° C, and the solution was stirred for 24 hours. The glucose isomerase crystals were separated by means of a Westfalia NA-7 separator. The yield was 390 kg of crystal mass having a dry solids content of 23.6 percent by weight and an activity of 2,300,000,000 GIU. 30 kg of sodium chloride and 180 kg of glucose were added to the crystal mass and the pH of the enzyme concentrate obtained was adjusted, by means of a 5% NaOH solution, to 7.0. Under these conditions the glucose was partly isomerized. In this way, 600 kg of stable enzyme concentrate was obtained, the composition of which was as follows:
- 49.7 wt. % water
- 30.0 wt. % sugars (glucose/fructose)
- 12.8 wt. % enzyme
- 2.5 wt. % ammonium sulfate
- 5.0 wt. % sodium chloride The glucose-isomerase activity of the enzyme concentrate was 3400 GIU/g.

EXAMPLE 4

An ultrafiltered fermentate was prepared in the way described in Example 1. For the crystallization of the glucose isomerase 4000 litres of ultrafiltered fermentate, having an activity of 2,400,000,000 GIU was used. The pH of the solution was adjusted by means of a 5% NaOH solution to pH 7.0. The temperature of the solution was adjusted to 12° C. For the crystallization of the glucose isomerase, 500 kg of ammonium sulfate dissolved in 750 liters of water was added to the solution during two hours with an even rate of feed. The solution was then cooled to −2° C, and stirred for 24 hours. The glucose isomerase crystals were separated by decanting. The yield was 230 kg of a crystal mass, having a dry solids content of 40.0 per cent by weight and an activity of 2,300,000,000 GIU. To the crystal mass 115 kg of glucose and 115 kg of fructose as well as 50 kg of invert sugar having a dry solids content of 70% were added. In this way, 510 kg of an enzyme preparation was obtained, the composition of which was as follows:
- 30.0 wt % water
- 52.0 wt % sugars (glucose, fructose)
- 15.1 wt % enzyme
- 2.9 wt. % ammonium sulfate.

The glucose-isomerase activity of the enzyme concentrate was 4500 GIU/g.

EXAMPLE 5

An ultrafiltered isomerase concentrate was prepared in the way described in Example 1. 50 g of ammonium sulfate was added to 0.95 litre of an isomerase concentrate having an activity of 600 GIU/ml and a temperature of 25° C. No precipitate was formed in the solution at this stage. The solution was cooled during 16 hours to 0° C, and it was kept at that temperature under gentle stirring constantly.

The isomerase started crystallizing in two days, and the crystallization continued so that after five days, 97.5 percent by weight of the isomerase was in crystalline form and 2.5 percent by weight still in dissolved form in the mother liquor. The crystals were separated from the solution by means of a laboratory centrifuge. Thereby 56 grams of wet crystal mass was recovered.

In accordance with this example, it is possible to crystallize the isomerase with a very low ammonium sulfate concentration as compared with the typical quantities that are known from the literature. At the same time, this is an example of pure cooling crystallization. In the light of this example, it is readily understandable that, if the precipitation by means of ammonium sulfate is carried out rapidly and, then the precipitate is separated by means of a centrifuge immediately, e.g. in 15 minutes, as is the case in the process of the U.S. Pat. No. 4,237,231, the isomerase remains completely in the solution, when ammonium sulfate concentration is low, and, if it precipitates, the crystallization will not be observed and its advantages unutilized. A crystal mass prepared in accordance with the present example can be dissolved exactly in the same way as in the other examples.

Concentrates prepared by the process of the instant invention have been shown to be stable to microbial and chemical inactivation for periods of time of up to 10 months.

What is claimed is:

1. A stable glucose isomerase concentrate comprising glucose isomerase of about 5 to about 20 percent by weight disssolved in a concentrated aqueous polyhydroxy compound containing solution of about 30 to about 60 percent by weight at a pH of from about 5 to about 8.

2. The concentrate according to claim 1, wherein said glucose isomerase content is from about 5 to about 15% and said pH is from about 6 to about 8.

3. The concentrate according to claim 2, including a salt at a concentration of not more than about 15 percent by weight.

4. The concentrate according to claim 3, wherein said salt is ammonium and/or magnesium sulfate.

5. The concentrate according to claim 1 wherein said polyhydroxy compound is selected from the group consisting of glucose, maltose, fructose, saccharose, sorbitol, xylitol or mixtures thereof such as invert sugar, glucose syrup or isomerized glucose syrup.

6. The concentrate according to claim 1 characterized by containing 50 percent by weight of glucose and fructose, 15 percent by weight of glucose isomerase, 5 percent by weight of ammonium or magnesium sulfate and 30 percent by weight of water.

7. The concentrate according to claim 1 characterized by containing 50 percent by weight of a mixture of glucose and fructose, 6.7 percent by weight of glucose isomerase, 3.5 percent by weight of ammonium sulfate and 39.8 percent by weight of water.

8. Process for the preparation of a stable glucose isomerase concentrate containing glucose isomerse dissolved in a concentrated aqueous polyhydroxy compound containing solution, comprising:
   (a) adding a suitable salt at a concentration of about 17 weight percent or less to a partially purified glucose isomerase solution obtained from fermentation, so as to crystallize the glucose isomerase at temperature of about 20° C or less;
   (b) cooling the solution so as to promote crystallization of the glucose isomerase, and separating the crystal mass formed, and
   (c) adding a polyhydroxy compound or a concentrated aqueous solution thereof to the obtained crystal mass, which dissolves, whereby a stable glucose-isomerase concentrate of about 5 to 20 perecent by weight and of about 30 percent to about 60 percent by weight of polyhydroxy compound is obtained.

9. The process according to claim 8, wherein the glucose isomerase is partially purified by ultrafiltration.

10. Process as claimed in claim 9, characterized by:
   (a) adding crystalline ammonium sulfate and then a water solution of ammonium sulfate to the ultrafiltered glucose isomerase obtained from fermentation so as to crystallize the glucose isomerase;
   (b) cooling the solution obtained so as to promote the crystallization of the glucose isomerase, separating the crystal mass formed, recrystallizing the crystals by dissolving them into water, filtering the solution formed, adding crystalline ammonium sulfate and a water solution of ammonium sulfate, and then separating the crystal mass formed, and
   (c) adding crystalline fructose to the crystal mass obtained, which dissolves, whereby a stable concentrate of glucose isomerase is obtained.

11. The process according to claim 10, wherein said recrystallization is performed one or more times.

12. Process as claimed in claim 9, characterized by:
   (a) adding magnesium sulfate and ammonium sulfate to the ultrafiltered glucose isomerase solution obtained from fermentation so as to crystalize the glucose isomerase;
   (b) cooling the solution so as to promote the crystallization of the glucose isomerase, separating the crystals formed by decanting, recrystallizing the crystals by adding water, magnesium sulfate and ammonium sulfate, separating the crystals by decanting, adjusting the pH to 6.5 by adding dilute ammonia, and crystallizing once more by adding magnesium sulfate and ammonium sulfate, whereby a crystal mass is obtained, and
   (c) adding glucose and fructose as well as water to the crystal mass, which dissolves, whereby a stable concentrate of glucose isomerase is obtained.

13. Process for crystallizing glucose isomerase comprising:
   (a) adjusting the pH of a partially purified glucose isomerase preparation to a range from about 5.7 to about 8.0;
   (b) cooling the preparation to about 16° C. or below;
   (c) adding ammonium and/or magnesium sulfate at a concentration from about 50 to about 170 g. per liter of preparation;
   (d) cooling to near the freezing point of the mixture to facilitate crystal formation.

14. The process according to claim 13, which includes separating the crystals from the solution.

15. The process according to claim 14, wherein crystallization is repeated by dissolving the separated crystals in a quantity of water of about 4 to 10 times the weight of the crystal mass at a temperature of about 20°-30° C., and repeating the steps of claim 14.

16. The process according to claim 13, wherein step (c) is performed gradually and ammonium and/or magnesium sulfate is added in solid and/or liquid form.

17. The process according to claim 13, where step (d) is performed concomitantly with step (c).

18. The process for crystallizing glucose isomerase comprising:
   (a) providing a glucose isomerase preparation obtained from lysed microbial cells and subjected to ultrafiltration;
   (b) adjusting the pH to about 7.0;
   (c) cooling the preparation to about 16° C. or below;
   (d) adding ammonium and/or magnesium sulfate in an amount from about 50 to 170 g. per liter of preparation over a period of from about 2 to about hours during which time the mixture is further cooled to near the freezing point of the mixture to facilitate crystal formations.

* * * * *

UNITED STATES PATENT AND TRADEMARK OFFICE
CERTIFICATE OF CORRECTION

PATENT NO. : 4,699,882
DATED : October 13, 1987
INVENTOR(S) : Kalevi J. Visuri

It is certified that error appears in the above-identified patent and that said Letters Patent is hereby corrected as shown below:

Column 3, line 46: "activity is to 5000 GIU/g" should read as --activity is 2000 to 5000 GIU/g--

Column 6, line 28: "0 02 moles" should read as --0.02 moles--

Signed and Sealed this

Thirty-first Day of May, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,699,882

DATED : October 13, 1987

INVENTOR(S) : Kalevi J. Visuri

It is certified that error appears in the above-identified patent and that said Letters Patent is hereby corrected as shown below:

Column 3, line 53: "10 wt. % water" should read as --30 wt. % water--

Column 10, line 57: "2 to about hours" should read as --2 to about 4 hours--

Signed and Sealed this

Twenty-third Day of August, 1988

*Attest:*

DONALD J. QUIGG

*Attesting Officer*      *Commissioner of Patents and Trademarks*